United States Patent [19]

Verunica

[11] 4,426,310

[45] Jan. 17, 1984

[54] LOW-IRRITATION SHAMPOO

[75] Inventor: Pierre M. Verunica, Lane Cove, Australia

[73] Assignee: Colgate-Palmolive Company, New York, N.Y.

[21] Appl. No.: 359,737

[22] Filed: Mar. 19, 1982

[51] Int. Cl.$^3$ .......................... C11D 1/29; C11D 1/62; C11D 1/94; A61K 7/08

[52] U.S. Cl. .................................... 252/106; 252/121; 252/173; 252/174.22; 252/546; 252/551; 252/552; 252/557; 252/DIG. 13; 424/70

[58] Field of Search ........... 252/106, 121, 173, 174.22, 252/546, 551, 552, 557, DIG. 13; 424/70

[56] References Cited

U.S. PATENT DOCUMENTS

| | | | |
|---|---|---|---|
| 3,697,220 | 10/1972 | Schwartz | 252/106 |
| 3,928,251 | 12/1975 | Bolich, Jr. et al. | 252/545 |
| 3,950,417 | 4/1976 | Verdicchio et al. | 252/547 |
| 3,962,418 | 6/1976 | Birkofer | 424/70 |
| 4,177,171 | 12/1979 | Walts | 252/546 |
| 4,256,611 | 3/1981 | Egan et al. | 252/551 |
| 4,261,851 | 4/1981 | Duke | 252/174.22 |

*Primary Examiner*—John E. Kittle
*Assistant Examiner*—Robert A. Wax
*Attorney, Agent, or Firm*—Richard N. Miller; Murray M. Grill; Herbert S. Sylvester

[57] ABSTRACT

A mild, neutral, clear shampoo which does not cause a burning sensation when an aqueous solution thereof is brought into contact with children's eyes, includes certain proportions of five different types of surface active agents in an aqueous medium. Preferred embodiments of the surface active agents are sodium lauryl diethoxy ether sulfate, polyethoxylated (78 EtO) glyceryl monoester of coconut oil fatty acids, polyoxyethylene (20 EtO) sorbitan monooleate, N,N-dimethyl-N-lauryl betaine and disodium lauryl diethoxy sulfosuccinate. Such shampoos also preferably include small proportions of sodium chloride, bactericide, perfume and neutralizing agent, when appropriate. Also within the invention is a method for manufacturing the shampoo.

7 Claims, No Drawings

LOW-IRRITATION SHAMPOO

This invention relates to a mild, neutral shampoo. More particularly, it relates to such a shampoo which does not cause a burning sensation when an aqueous solution thereof is brought into contact with children's eyes.

Liquid shampoos based on aqueous solutions, emulsions and other dispersions of soaps in water have long been used. Such shampoos, to be made clear in appearance often require the presence of a cosolvent, such as alcohol, in the aqueous medium. However, such cosolvents are sometimes drying to the hair and scalp. Clear shampoos based on synthetic organic detegents or surface active agents have been manufactured and have to a substantial extent supplanted competitive preparations based on alkali metal soaps of higher fatty acids. Often, for good foaming, lathering and cleaning properties, such shampoo formulations have included anionic synthetic organic surface active agents (including detergents). However, shampoos based on either anionic synthetic organic surface active agents or soaps tend to be irritating to the human eye and such characteristic of these products is especially disadvantageous when they are intended for use in washing babies' and children's hair.

Although nonionic, amphoteric, ampholytic and zwitterionic surface active agents may not be as irritating to the human eye as their usual anionic counterparts, shampoos based on such materials are often of insufficient foaming and lathering powers and sometimes may also be poorer cleaning agents. Therefore, it has been found desirable to include some anionic detergent or surface active agent in most shampoos, even those intended for washing children's hair (and therefore possibly coming into contact with the eyes). However, if anionic surfactant is present it can make the shampoo unacceptable for marketing as a children's or baby shampoo due to the ocular irritation characteristics thereof. Therefore, extensive research has been undertaken in efforts to discover shampoo formulations which would not be irritating to the human eye and yet, would be of satisfactory foaming, lathering and cleaning properties and would possess other acceptable physical characteristics, including viscosity and appearance.

Some allegedly satisfactory shampoos have been made from mixtures of particular types of anionic, zwitterionic (or amphoteric or ampholytic) and nonionic surfactants and in some cases an amphoteric-anionic surfactant has been employed in such formulations in place of the mixture of amphoteric and anionic surfactants. For examples of such compositions, see U.S. Pat. Nos. 3,928,251, 3,950,417, 3,962,418 and 4,177,171. Other disclosures considered relevant are British patent specification Nos. 1,508,929, 1,540,301 (like U.S. Pat. Nos. 4,177,171) and 2,026,532, and French Pat. No. 1,403,213.

As is evident from the prior art, to make a shampoo composition of low eye irritation properties it is not enough merely to mix together a plurality of types of surface active agents. As has been shown by the present inventor's experimentation and as is deduced from the art, to obtain a satisfactorily mild shampoo, relatively limited proportions of particular types of surfactants should be employed and sometimes minor changes in the type of one component of such a shampoo or in the proportion of one such component present may mean the difference between an acceptable irritation-free product and one which causes pain to a baby or child, whose hair is being shampooed, when an aqueous solution of the shampoo accidentally comes into contact with his or her eyes.

The present invention is of a novel and unobvious mild shampoo which does not cause a burning of children's eyes upon contact therewith. It is a novel composition and it is considered that the described combination of the plurality of surfactants present therein in proportions within the ranges given is unobvious, especially in view of the fact that various other combinations of anionic, amphoteric and nonionic detergents, especially those containing similar proportions of anionic detergents, are unacceptably harsh to the eyes.

In accordance with the present invention a mild shampoo, the pH of which is in the range of 6 to 8, preferably in the range of 6 to 7 and more preferably, about 7, and aqueous solutions of which do not cause a burning sensation when brought into contact with children's eyes, comprises (A) an alkali metal higher alkyl poly-lower alkoxy ether sulfate, (B) a polyethoxylated glyceryl higher fatty acid monoester of from 60 to 100 moles of ethylene oxide per mole, (C) a polyoxyethylene sorbitan monooleate of 10 to 30 moles of ethylene oxide per mole, (D) an N-higher alkyl betaine and (E) an alkali metal higher alkyl poly-lower alkoxy sulfosuccinate, in an aqueous medium, and in which the proportion of the total of A, B, C, D and E to the aqueous medium is in the range of 1:3 to 1:9 and the relative proportions of A, B, C, D and E are 2.5 to 5, 1.5 to 4.5, 1.5 to 3.5, 1.0 to 3.0 and 1, respectively. Also within the invention is a method of manufacturing such a shampoo.

The surfactant designated A is an alkali metal higher alkyl poly-lower alkoxy ether sulfate, which is anionic in nature. In this specification, in accordance with ordinary usage in the detergent art, "higher", as applied to alkyl, indicates the presence of from 8 to 20 carbon atoms, often preferably 8 or 10 to 18 carbon atoms. The alkali metal is sodium or potassium and more commonly, often for reasons of economy, is sodium, although potassium salts may be more soluble in water. The higher alkyl of this anionic surfactant is preferably of 10 to 14 carbon atoms and most preferably is lauryl. The poly-lower alkoxy may be a poly-lower ethoxy or poly-lower propoxy, usually of 1 to 3 or 4 moles of lower alkylene oxide per mole, and most preferably is diethoxy. Such material is sold by Henkel & Cie. in combination with component E, under the trademark Texapon SBN. Component B is a polyethoxylated glyceryl higher fatty acid monoester of from 60 to 100 moles of ethylene oxide per mole, preferably 70 to 90 moles per mole and most preferably about 78. As with the "higher" alkyl, the "higher" fatty acid of the higher fatty acid monoester may also be 8 to 20 carbon atoms, preferably 8 or 10 to 18 and more preferably 8 or 10 to 16 carbon atoms, with coconut oil fatty acids (which may be hydrogenated in some cases) being preferred. This nonionic surfactant is available from Sherex Chemical Company and is sold as Varonic L167.

The polyoxyethylene sorbitan monooleate of 10 to 30 moles of ethylene oxide per mole, which is component C, another nonionic surfactant, will preferably contain from 16 to 24 moles of ethylene oxide per mole and more preferably is of about 20 moles per mole. It is available from Atlas Chemical Company as Tween 80. The zwitterion component, D, is an N-higher alkyl betaine, and while "higher" with respect to alkyl, may have the meanings previously given, preferably the alkyl will be of 8 to 16 carbon atoms and most preferably it is coconut oil derived alkyl or lauryl. The nitrogen of the betaine is also often mono or disubstituted, preferably disubstituted, with lower alkyls of 1 to 4 or 1 to 3 carbon atoms, most preferably each being methyl. In some instances an equivalent betaine may be substituted and one of those which may be used, in whole or in part, e.g., 10 to 90% replacement, is a coconut oil fatty acids amidopropyl betaine. Such products are available from Henkel & Cie. under the trade names Dehyton AB30 and Dehyton AB30A or Dehyton K. Also considered to be useful is a similar material sold under the trade name Tego Betaine L7 by Goldschmidt Products Corp. The last two types facilitate the manufacture of clear shampoos having lower cloud points.

Component E is an alkali metal higher alkyl polylower alkoxy sulfosuccinate, wherein the alkali metal, higher alkyl and lower alkoxy are of the meanings previously given, with the alkali metal being sodium or potassium, normally preferably disodium, the higher alkyl preferably being of 10 to 14 carbon atoms and most preferably being lauryl, and the lower alkoxy being ethoxy or propoxy, with 1 to 3 or 4 moles, preferably of ethylene oxide, per mole and most preferably being diethoxy. The preferred material is preferably present with component A and is commercially available under the trademark Texapon SBN, previously mentioned. In some instances the Texapon SBN has been replaced completely by an equivalent amount of Texapon ASV and, when considered desirable, it may be partially replaced thereby, e.g., 10 to 40% replacement, and the product will have the advantage of even lower eye irritation properties. However, in such circumstances the product viscosity will sometimes be lowered and addition of thickening agent may be desirable to obtain a satisfactory viscosity. Such thickening agents, in addition to other effects they may have on the formulation, can increase the eye irritation index and therefore their use will often be avoided. For such reasons the employment of a mixture of anionic surfactant components A and E, as in Texapon SBN, is preferred.

The surface active agents described above are dissolved in an aqueous medium and at room temperature produce a clear liquid shampoo of desirable viscosity and neutral pH. The aqueous medium, while it may contain various other constituents and adjuvants in relatively minor proportions, and may in certain circumstances contain cosolvents, such as ethanol and/or isopropanol in small quantities (in which cases thickening materials may sometimes be used to counteract the thinning effects of the solvents), will preferably be water, with only minor proportions of adjuvants therein (and no cosolvents and supplementary thickeners). While normal city water may be employed, with hardnesses in the normal range, usually no greater than 150 parts per million as calcium carbonate, preferably the hardness will be low, usually no more than 125 or 75 p.p.m., and more preferably, the water employed will be distilled or deionized. Most preferably, the water will be deionized and irradiated.

To help to adjust the electrolyte content of the shampoo and to control the viscosity thereof there may be present in it a small proportion of an appropriate water soluble salt. It has been found that sodium chloride is most satisfactory for this purpose but it is considered that other water soluble salts, including potassium chloride, sodium sulfate, potassium sulfate and equivalents, may also be employed.

While it may not be necessary to utilize any bactericidal additives in the present shampoo, as a safety measure, considering the organic content thereof, a small proportion of a suitable antibacterial material may be employed. Formaldehyde, phenolics and parabenzoic acid derivatives can be used in ordinary shampoos but because of skin penetrating effects, toxicity or low water solubility, are not as suitable for baby shampoos as is N-(3-chloroallyl)-hexaminium chloride, also known as Quaternium-15 (CAS. No. 4080-31-3), other names and properties of which are given in the Merck Index, 9th edition, at page 268. Such material is available commercially from Dow Chemical Company under the trademark Dowicil 200.

As is well known, to make shampoos aesthetically desirable they will usually be appropriately perfumed and colored. Any of a wide variety of perfumes may be employed and while some of these may be at least partially soluble in water, usually the most desirable are lipophilic and hydrophobic and therefore they are usually emulsified in opaque or emulsion shampoos. However, they may be solubilized by cosolvents in aqueous shampoos which are to be marketed clear. The appropriate components of the preferred lipophilic perfumes which may be incorporated in the present shampoos, which may include known perfume ingredients such as flower oils, essential oils, isolates, synthetics, extracts, resinoids and balsams, are found to be solubilized in the small quantities employed in the present shampoos without the use of a cosolvent and do not cloud the shampoo at normal use temperatures. Among the various components of perfumes which are soluble in the present shampoos may be mentioned, for example, rose and jasmine oils, sandalwood and citrus oils, geraniol and citral, esters and synthetic musks. Coloring of shampoos is usually desirable and this may be effected by the use of nontoxic dyes, such as those identified by F.D. & C. colors and numbers, e.g., F.D. & C. Yellows No's. 5 and 6.

To neutralize the shampoo, if it is not of a pH about 7, any of various suitable neutralizing agents may be employed but it is preferred to utilize citric acid, usually in the form of its hydrate, or sodium hydroxide, as appropriate. Although other acceptable neutralizing agents can be substituted, citric acid is preferable because it has sequestering powers and sodium hydroxide is preferred because it adds only sodium ion to the system and does not produce any gaseous byproducts.

The mentioned components and equivalents thereof are the only materials present in the preferred embodiment of this invention but it is considered that relatively minor modifications of the formulation can be made and acceptable and non-interfering adjuvants may be employed in limited proportions. For example, in some circumstances supplementary solubilizers and/or antifreeze agents, such as lower alkanols or polyols, may be utilized. Hair conditioning agents, fluorescent brighteners, foam stabilizers and fungicides may also be used, but are not necessary and may sometimes be undesirable in the invented compositions.

Various thickening agents often used in the art may be incompatible with the betaine surfactant, so the self-thickening action of the betaine compound of the present shampoos is especially useful. At a pH below 7 the composition becomes more viscous, as acidity increases, and the reverse is true above such pH, the shampoo becoming thinner as pH increases. Thus, most desirable pH's are in the 6–7 range.

To obtain the desired mild neutral shampoo which does not sting the eyes when aqueous solutions thereof may accidentally contact them it is important that the various described surface active agent components of the invented composition be present in proportions within specified ranges. Otherwise, burning of the eyes may result, the shampoo may be objectionably cloudy at normal use temperatures and the shampoo viscosity may be unacceptable. Normally, the pH of the shampoo should be in the range of 6 to 8, preferably 6 or 6.5 to 7 or 7.5 and most preferably 7 or about 7, and the shampoo should be free flowing but sufficiently thick so that it does not run off the hair, when applied to it in normal manner. Usually the shampoo should have a viscosity of at least 300 centipoises at 25° C., preferably at least 400 centipoises at such condition. Ranges of viscosity, for example, will usually be from 300 to 600 centipoises and preferably the viscosity is of 400 to 500 centipoises, at 25° C., measured in the manner to be described in conjunction with the working examples to follow. Although cloudy, translucent, pearlescent and opaque shampoos may be intentionally made by modifications of the formula of this invention, usually it will be desired that the shampoo be transparent and sparkling in appearance. Such a shampoo will normally be light in color and usually it will be possible to read, through a clear bottle and the shampoo contained therein, indicia on the "inside" of a label applied to such bottle. While absolutely clear shampoo solutions are preferred, it is also intended that the present invention apply to apparently clear liquids exhibiting the Tyndall effect. The shampoos of this invention are not irritating to the skin nor are they ocular irritants, and aqueous solutions thereof, of shampoo concentrations in the range of 0.1 to 100% (although normally concentrations are in the range of 0.1 to 10%) do not cause a stinging or burning sensation in the eyes and do not cause irritation thereof or the appearance of such irritation.

The various desirable properties of the present shampoo that were mentioned above are attributable to the employment of the mentioned shampoo components in the aqueous medium in proportions within the rather narrow given ranges. Thus, such proportions of the surface active agents identified as A, B, C, D and E are in the "ranges" of 2.5 to 5, 1.5 to 4.5, 1.5 to 3.5, 1.0 to 3.0 and 1 (1 not being a true range but serving as a base component), respectively, with the proportion of the total of A, B, C, D and E to the aqueous medium being in the range of 1:3 to 1:9. Preferred ranges of A, B, C, D and E are 3 to 4.5, 2 to 4, 2 to 3, 1.3 to 2.3, and 1, respectively. On a percentage basis, percentages of A, B, C, D, E and medium are normally in the ranges of 5 to 8, 4 to 6, 3 to 5, 2.5 to 4, 1 to 1.5 and 70 to 84.5, respectively, with most preferred percentages being 6.5, 4.9 4.1, 3.1, 1.8 and the balance of water or aqueous medium. The aqueous medium may contain from 1 to 3% of sodium chloride, 0.1 to 1% of lipophilic perfume, 0.001 to 0.2% of dye, 0.01 to 0.2% of antimicrobial agent, e.g., 0.02 to 0.1% of bactericide, and 0 or 0.01 to 1% of acidic and/or basic neutralizing agent(s). In most preferred formulations the percentages of salt and lipophilic perfume will be about 2 and 0.4, respectively, and percentages of antimicrobial agent and neutralizer(s) are small or nil, so that the water content will be about 77.2%.

Although various mixtures of different types of detersive materials have been made in an effort to produce satisfactory eye sting-free baby shampoos, the present composition is novel and the success thereof is based upon the employment of the certain described components in the mentioned proportions. Thus, while it is known that anionic detergents do tend to cause stinging or a burning feeling in the eyes when aqueous solutions thereof are brought into contact with the eyes, and although the anionic detergents presently employed, comparatively mild as they are, do cause such a stinging when used alone or with each other in the present formulations, apparently due to interactions with the other detersive components they are not objectionable and the final shampoo product of this invention does not cause such a burning sensation. The mentioned anionic surface active agents, A and E, contribute good detergency, foaming, lathering and satisfactory viscosity, and due to their good foaming characteristics they allow the making of a mild shampoo which does not require the inclusion of fatty acid alkanolamides or similar materials as thickeners and foam boosters (and thereby the irritation accompanying use of such additives is also avoidable). The zwitterionic component, D, helps to improve hair conditioning and combability and also is a satisfactory detergent and foaming agent (it boosts the foaming power of A, B and E) of low eye sting and irritation characteristics. Although to some extent ampholytes may tend to react with anionics to form insolubles, in the present compositions clear shampoos result, with cloud points in the region close to 0° C., normally being below 8° C., e.g., about or below 6° C. The particular nonionic surfactants, B and C, are important for detergency, water solubility and compatibility with the other components of the shampoos but in addition to these characteristics B is also important for its action in diminishing any eye irritation that might otherwise result from the anionic detergents and because it helps to thicken the shampoo, thus allowing the omission of other thickeners, which might be incompatible. The irritation reducing characteristic is not typical of other polyethoxylated polyol higher fatty acid esters and it appears that the unexpectedly beneficial properties of B in the present shampoos are dependent on the particular proportion of ethylene oxide contained in the glyceryl monoether of the type shown (although applicant does not intend to be limited by such theory). Component C also helps to improve the utility and appearance of the present shampoos by maintaining the desirable clarity thereof. One way in which this is accomplished, apparently, is by aiding in the solubilization of lipophilic materials present, such as perfume, in the product.

From the above discussion it is evident that the very desirable and important characteristics of the present mild and painless shampoos result from the novel combination of materials in the described proportions and from the interrelationships and interactions of such components, which result in a mild shampoo of neutral pH, clear in appearance and painless to the human eyes when aqueous shampoo solutions accidentally come into contact with them. Yet, such shampoos are excellent detergents, leave the hair in desirably manageable and combable condition, and are of acceptable viscosities and of attractive appearances (preferably clear).

In the manufacture of the described shampoos it is important to begin with the heating of component B, which is normally solid, to a temperature at which it is liquid, which temperature will normally be within the range of 40° or 42° to 55° C., preferably, about 45° C., heating a substantial proportion of the final shampoo weight of water, usually about 45 to 60%, such as about 54%, to a temperature in the same range and preferably to the same temperature, mixing the liquefied component B and the heated water, usually in the final mixing tank, until the mixture becomes clear, and then admixing sequentially with the clear mix, which is at a temperature in the range of 20° to 45° C., components A, E, D and C, which are also at a temperature in such 20° to 45° C. range. When A, E and D are so admixed, they are in liquid form and in aqueous media and component C is also in liquid form (but is all active ingredient). In a preferred embodiment of the inventive process components A and E are present together in an aqueous medium at a total (A+E) concentration of about 25 to 35% when they are admixed with the clear solution of component B in the "initial" aqueous medium. Component D is also present in an aqueous medium at a concentration of about 25 to 35% when admixed with the aforementioned materials.

When (and if) the shampoo is being perfumed, preferably with 0.1 to 1% of a lipophilic perfume, e.g., about 0.4%, such perfume will be mixed with component C before the mixing of C with other composition constituents, and such pre-mixing will be at a temperature in the range of 20° to 35° C. and the temperature of the other shampoo components when such sub-mixture is admixed with them will also be in such range, to minimize losses of volatiles from the perfume and to help to maintain the clarity of the champoo. Addition of a salt to the shampoo, such as the addition of from 1 to 3% of sodium chloride, e.g., 2% thereof, is preferably effected by first wetting the sodium chloride, in particulate solid form, with a portion of the aqueous solution of components A and E, and incorporating such wetted material in the shampoo at an appropriate time, preferably after all of the surfactants are present. Other adjuvants may be added at any appropriate time in the manufacture of the shampoo, preferably after all the surfactants are present, with care being taken in all such cases to minimize the possibility of cloudy shampoos being made due to failure to dissolve such adjuvants or due to precipitating out of materials from the shampoo during such additions. For shorter batch times and to ensure complete solubilization of Dowicil 200, when present, such powder material should be premixed with component C, after which perfume can be added to the mixture. Dowicil 200 can also be wetted with a small portion of the mixture from the main batch. Direct addition of such antibacterial agent, while possible, may require longer mixing periods and accordingly, direct mixing is usually avoided.

After completion of the manufacture of the shampoo the pH thereof may be tested and may be adjusted, as desired, by addition of appropriate neutralizing agent(s), preferably citric acid and/or sodium hydroxide. Normally the additions will be in the liquid state with respect to sodium hydroxide and as finely divided particulate solids for the citric acid but citric acid solutions may also be employed.

By following the manufacturing method described clear stable shampoos can be made whereas when the method is modified significantly the risk of obtaining cloudy or unattractive products can be substantially increased.

The following examples illustrate a preferred embodiment of the invention but are not intended to be limiting. Unless otherwise indicated, all parts are by weight and all temperatures are in °C.

EXAMPLE 1

| Constituent | Parts by Weight |
|---|---|
| Deionized water (irradiated) | 53.548 |
| Varonic L167 | 5.000 |
| Texapon SBN | 25.000 |
| Dehyton AB30 | 10.000 |
| Tween 80 | 4.000 |
| Perfume | 0.400 |
| Dowicil 200 | 0.050 |
| Salt | 2.000 |
| F. D. & C. Yellow dye No. 5 | 0.002 |
| | 100.000 |

The deionized water employed is city water of a hardness of approximately 100 p.p.m., as calcium carbonate, irradiated with ultraviolet light for sterilization. The Varonic L167 of the chemical formula previously described, 99+% active, in hard solid form at room temperature with a melting point of approximately 42° C., a pH of 6.5 in distilled water at 1% concentration therein, of a Gardner Color of 2 and of an HLB number of 18. The Texapon SBN is of a percentage activity in the range of 30 to 34%, e.g., 32–34%, and at room temperature is a clear pale yellow viscous liquid with a slight pungent odor. Its cloud point is below 0° C., its viscosity at 20° C. is approximately 8,000 centipoises and its pH in distilled water (10% solution) is in the range of 6 to 7. The parts of components A and E therein are about 6.5 and 1.7, respectively. The Dehyton AB30 is a 30% aqueous solution of the coconut oil fatty acids dimethyl betaine compound, which is in the form of a practically odorless, clear, pale yellow liquid at room temperature, with a cloud point below −5° C. and a pH, in distilled water (10% solution) of approximately 7. Tween 80 is a neutral light colored 100% active ingredient liquid. Dowicil 200 is N-(3-chloroallyl)-hexaminium chloride, in the form of a 100% active antibacterial powder, and the salt employed is one commonly known as dairy salt, which is a purer form of table salt, having a water insolubles content less than 0.5% and forming clear aqueous solutions. The dye is in an aqueous solution but is shown in the formula as a solid (100% active) material, for convenience.

A shampoo of the above formulation is made by pumping the 53.548 parts of water into a mixing vessel fitted with heating and agitation means and heating it to 45° C. Simultaneously, the 5.000 parts of Varonic L167 are added to a jacketed heating kettle and heated to 45° C., at which temperature (or slightly below such temperature) the Varonic L167 melts. Then it is pumped into the first mixing vessel and is mixed in with the heated water until the mixture becomes clear, at which point heating is halted. Additions of the formula amounts of Texapon SBN, Dehyton AB30 and Tween 80 then follow, with the Tween 80 addition being after a pre-mix of that material with the perfume at a temperature of 35° C. or lower, and with the addition of the pre-mix to the other components being at a temperature of about 30° C. Next, the Dowicil 200, salt and dye are added, with the Dowicil 200 and salt being wetted with a small portion of the mix before further admixing, which promotes easier dispersion and solution. The pH is then checked and is found to be in the range of 6.5 to 7, so no correction thereof is required.

The shampoo made is clear and of a viscosity in the range of about 400 to 500 centipoises, measured using a Brookfield LVT Viscosimeter, with spindle No. 2 at speed 60, and has a cloud point of about 6° C. The active ingredient content of the product is about 20.4% surfactant. The shampoo is non-irritating to the eyes and does not cause smarting, burning or stinging sensations therein when brought into contact with them in concentrated form or after being diluted in water, as during shampooing. On the contrary, when other detergent mixtures are employed, even those containing nonionic and zwitterionic detergents as well as anionic detergents, ocular irritation may occur, as for example, when a small quantity, e.g., 3 to 10%, of lauric myristic diethanolamide is present and/or when the Varonic L167 is omitted.

In modifications of the above product Dehyton AB 30A, sometimes referred to as Dehyton K, is substituted for Dehyton AB 30 and in other experiments Tego Betaine L7 replaces Dehyton AB 30. In both such cases the shampoo made is clear and when stored at 4° C. for a period of eight weeks, is still clear. In other experiments Texapon ASV is employed in place of Texapon SBN and excellent ocular non-irritation properties result, although more salt is utilized in such formulation to maintain desired viscosity and consequently, somewhat poorer foaming characteristics result.

EXAMPLE 2

The product of the formula of Example 1 is made by the method described in such example but a slightly different color is obtained by utilization of an additional 0.0006 part of F. D. & C. Yellow dye No. 6 and subsequent additions of minor proportions of citric acid monohydrate and 19.0% $Na_2O$ content aqueous sodium hydroxide solution (up to 1 part each, preferably less than 0.5 part total). The final pH is 7.0, the product viscosity, measured by the method described in Example 1, is within the range of 400 to 500 centipoises and the cloud point is 6° C.

The product of this example is tested for eye irritation, primary skin irritation and oral toxicity and is compared to a commercially successful "no-tears" baby shampoo. Both products were found to be non-irritating to the eyes by Draize eye tests, non-toxic according to $LD_{50}$ evaluations and not primary skin irritants, in tests carried out by independent consulting laboratories. According to several panel tests, in which more than 30 panelists evaluated the products, eye sting characteristics (if any) were considered to be about the same but the experimental product was generally preferred and was found superior in cleaning, combability of the hair, hair lustre and manageability of the hair.

In variations of this formula the dyes are changed, the salt content is decreased to 1% and the perfume is reduced to 0.2%, and final clear, mild and neutral products result, which do not irritate children's eyes. Also, the product viscosity can be altered when desired, being increased when the pH is lowered. However, when the proportions or percentages of the surfactants are changed so as to be outside the given ranges the products suffer in at least one of the recited desirable characteristics mentioned or otherwise are not benefited by addition(s) of such component(s).

EXAMPLE 3

| Constituent | Parts by Weight |
|---|---|
| Irradiated deionized water | 52.35 |
| Varonic L167 | 5.00 |
| Texapon SBN | 25.00 |
| Dehyton AB30 | 10.00 |
| Tween 80 | 4.00 |
| Perfume | 0.40 |
| Quaternium-15 | 0.05 |
| Iragon yellow LU dye (1% solution) | 0.20 |
| Dairy salt | 2.00 |
| | 99.00 |

A shampoo of the formula given above is made by the method described in Example 1, and the pH thereof is adjusted by addition of a 50% aqueous solution of citric acid until it is 6.63. At such pH the viscosity of the shampoo at 25° C., using a Brookfield LVT Viscosimeter, with Spindle No. 2 at 12 r.p.m., is 1,100 centipoises. The pH may be adjusted by addition of more of the citric acid solution or by the addition of a 1% aqueous sodium hydroxide solution, with the total of such solutions utilized being no more than about 1.00 part, until the desired pH and the desired viscosity are obtained.

Other than the higher viscosity, the shampoo has properties like those of the shampoos of this invention described in the previous working examples. It is an excellent cleaning agent for the hair and does not sting the eyes when it accidentally comes into contact with them. Also, it leaves the shampooed hair satisfactorily manageable and combable.

From the above information it will be evident that the products of this invention are useful mild, clear, neutral "no-tears" baby shampoos or children's shampoos which are non-toxic and non-irritating and which are of desirable cleaning, lathering, conditioning and combing properties, at least equal to and in several aspects superior to a successful commercial baby shampoo.

The invention has been described with respect to various examples and illustrations thereof but is not to be limited to these because it is evident that substitutes and equivalents may be employed without departing from the invention.

What is claimed is:

1. A method of manufacturing a mild shampoo, the pH of which is in the range of 6 to 8 and aqueous solutions of which do not cause a burning sensation when brought into contact with children's eyes, which shampoo comprises (A) an alkali metal higher alkyl polyethoxy ether sulfate, (B) a polyethoxylated glyceryl higher fatty acid monoester of from 60 to 100 moles of ethylene oxide per mol, (C) a polyoxyethylene sorbitan monooleate of 10 to 30 moles of ethylene oxide per mole, (D) an N-higher alkyl or alkylamidopropyl dimethyl betaine and (E) an alkali metal higher alkyl polyethoxy sulfosuccinate, in an aqueous medium, and in which the proportion of the total of A, B, C, D and E to the aqueous medium is in the range of 1:3 to 1:9 and the relative proportions of A, B, C, D and E are 2.5 to 5, 1.5 to 4.5, 1.5 to 3.5, 1.0 to 3.0 and 1, respectively, which comprises heating from 45 to 60% of the shampoo batch weight of water to a temperature in the range of 42° to 55° C., separately heating B to such a temperature, at which it is liquid, mixing such liquid B and water until such mixture appears clear, and admixing sequentially with such clear mix, which is at a temperature in the range of 20° to 45° C., A, E, D and C, which are at a temperature in the range of 20° to 45° C., with A, E and D being in aqueous media when so admixed.

2. A method according to claim 1 wherein the aqueous medium is water, A, B, C, D and E are sodium lauryl diethoxy ether sulfate, polyethoxylated glyceryl monoester of coconut oil fatty acids containing about 78 moles of ethylene oxide per mole, polyoxyethylene sorbitan monooleate of about 20 moles of ethylene oxide per mole, N,N-dimethyl-N-lauryl betaine and disodium lauryl diethoxysulfosuccinate, respectively, the percentages of which, and of water, in the shampoo are in the ranges of 5 to 8. 4 to 6, 3 to 5, 2.5 to 4, 1 to 2.5 and 70 to 84.5, respectively, B is a solid at room temperature and is essentially 100% of such active ingredient, A and E are present together in an aqueous medium at a total concentration of about 25 to 35%, D is present in an aqueous medium at a concentration of about 25 to 35%, and C is in the liquid state at room temperature and is essentially 100% of such active ingredient, the heating of the aqueous medium and B is to a temperature of about 45° C., 0.1 to 1% of a lipophilic perfume is mixed with C before mixing of C with other composition constituents, said mixing of perfume and C is at a temperature in the range of 20° to 35° C. and the temperature of the mixture of other shampoo constituents with which the mixture of C and perfume is mixed is in the range of 20° to 35° C.

3. A method according to claim 2 wherein from 1 to 3% of sodium chloride and from 0.01 to 0.2% of N-(3-chloroallyl)-hexaminium chloride were wetted with a portion of the aqueous solution of A, B, C, D and E and are incorporated in the shampoo by mixing with other components thereof.

4. A method according to claim 3 wherein the pH of the shampoo resulting is measured and, if outside the range of 6.5 to 7.5, is adjusted by addition of citric acid and/or sodium hydroxide so as to bring it into such range.

5. A mild, clear, liquid shampoo, the pH of which is in the range of 1 to 3, and aqueous solutions of which do not cause a burning sensation when brought into contact with children's eyes, which consists essentially of, by weight, (A) 5% to 8% of an alkali metal $C_{10}$–$C_{14}$ alkyl polyethenoxy ether sulfate containing from 1 to 4 moles of ethylene oxide, (B) 4% to 6% of a polyethoxylated glyceryl $C_8$–$C_{16}$ fatty acid monoester containing from 60 to 100 moles of ethylene oxide per mole; (C) 3% to 5% of a polyoxyethylene sorbitan monooleate of 10 to 30 moles of ethylene oxide per mole; (D) 2.5% to 4% of a zwitterionic detergent selected from the group consisting of N—$C_8$–$C_{16}$ alkyl dimethyl betaine, N—$C_8$–$C_{18}$ alkylamidopropyl dimethyl betaine and mixtures thereof; (E) 1% to 2.5% of an alkali metal $C_{10}$–$C_{14}$ alkyl polyethenoxy sulfosuccinate containing from 1 to 4 moles of ethylene oxide and (F) 70% to 84.5% of an aqueous medium, said shampoo having a viscosity at 25° C. in the range of 300 to 600 centipoises and a cloud point below 8° C.

6. A shampoo according to claim 5 wherein (A) is a sodium salt, D is said N-alkyl-dimethyl betaine and (E) is a sodium salt.

7. A shampoo according to claim 5 which includes, in addition, from 1% to 3% of sodium or potassium chloride and from 0.01% to 0.2% of N-(3-chloroallyl)-hexaminium chloride.

* * * * *